(12) United States Patent
Abels et al.

(10) Patent No.: US 9,107,725 B2
(45) Date of Patent: Aug. 18, 2015

(54) METHOD OF MANUFACTURING AN ORTHODONTIC BRACKET HAVING A LASER SHAPED GREEN BODY

(71) Applicant: Ormco Corporation, Orange, CA (US)

(72) Inventors: Norbert Abels, Homburg (DE); Claus H. Backes, Saarbrücken (DE)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 14/573,398

(22) Filed: Dec. 17, 2014

(65) Prior Publication Data

US 2015/0104345 A1    Apr. 16, 2015

Related U.S. Application Data

(60) Continuation of application No. 13/936,589, filed on Jul. 8, 2013, now Pat. No. 8,931,171, which is a continuation of application No. 12/940,679, filed on Nov. 5, 2010, now Pat. No. 8,479,393, which is a (Continued)

(51) Int. Cl.
*A61C 3/00* (2006.01)
*A61C 7/14* (2006.01)
*B22F 3/10* (2006.01)

(Continued)

(52) U.S. Cl.
CPC ... *A61C 7/14* (2013.01); *B22F 3/10* (2013.01); *B23K 26/365* (2013.01); *A61C 13/0022* (2013.01); *Y10T 29/49568* (2015.01); *Y10T 29/49995* (2015.01)

(58) Field of Classification Search
CPC ...... A61C 7/14; A61C 13/0022; B28B 11/12; B23P 15/00; Y10T 29/49568; Y10T 29/49567
See application file for complete search history.

(56) References Cited

U.S. PATENT DOCUMENTS

| | | | |
|---|---|---|---|
| 4,604,057 | A | 8/1986 | Viglietti |
| 4,661,059 | A | 4/1987 | Kanno |
| 4,842,513 | A | 6/1989 | Haarmann |

(Continued)

FOREIGN PATENT DOCUMENTS

| | | | |
|---|---|---|---|
| DE | 10041338 | A1 | 3/2002 |
| DE | 10258444 | A1 | 7/2003 |

(Continued)

OTHER PUBLICATIONS

D. Guo et al., A Novel Anti-Spatter and Anti-Crack Laser Drilling Technique: Application to Ceramics, Applied Physics A, vol. 76, pp. 1121-1124, Jan. 22, 2003.

(Continued)

*Primary Examiner* — Sarang Afzali
(74) *Attorney, Agent, or Firm* — Wood, Herron & Evans, LLP

(57) ABSTRACT

A green metal body includes metal particles and a binder in the shape of an orthodontic bracket and/or base plate. The green metal body is fabricated by being laser-cut with a laser to shape the green metal body into the shape of an orthodontic bracket and/or to carve recesses and/or undercuts into the bonding surface of the bracket. The green metal body is sintered to shrink its volume into a denser and less porous sintered metal body configured to be an orthodontic bracket. The resultant sintered orthodontic bracket includes recesses and/or undercuts in the bonding surface to provide a mechanical aspect when bonded to a tooth.

10 Claims, 4 Drawing Sheets

Related U.S. Application Data continuation of application No. 12/104,958, filed on Apr. 17, 2008, now abandoned, which is a division of application No. 11/193,239, filed on Jul. 29, 2005, now abandoned, which is a continuation-in-part of application No. 11/042,025, filed on Jan. 25, 2005, now abandoned.

(51) Int. Cl.
*B23K 26/36* (2014.01)
*A61C 13/00* (2006.01)

(56) References Cited

U.S. PATENT DOCUMENTS

| | | |
|---|---|---|
| 4,957,554 A | 9/1990 | Mathers et al. |
| 4,968,459 A | 11/1990 | Sernetz |
| 5,215,693 A | 6/1993 | Lee |
| 5,232,361 A | 8/1993 | Sachdeva et al. |
| 5,238,627 A | 8/1993 | Matsuhisa et al. |
| 5,242,298 A | 9/1993 | Sernetz |
| 5,267,854 A | 12/1993 | Schmitt |
| 5,267,855 A | 12/1993 | Tuneberg |
| 5,326,259 A | 7/1994 | Rohlcke et al. |
| 5,393,486 A | 2/1995 | Eckert et al. |
| 5,522,725 A | 6/1996 | Jordan et al. |
| 5,556,276 A | 9/1996 | Roman et al. |
| 5,589,430 A | 12/1996 | Krahn et al. |
| 5,595,484 A | 1/1997 | Orikasa et al. |
| 5,613,182 A | 3/1997 | Lynn |
| 5,613,849 A | 3/1997 | Tanaka et al. |
| 5,616,026 A | 4/1997 | Cash |
| 5,618,175 A | 4/1997 | Reher et al. |
| 5,622,494 A | 4/1997 | Andreiko et al. |
| 5,639,402 A | 6/1997 | Barlow et al. |
| 5,641,920 A | 6/1997 | Hens et al. |
| 5,678,162 A | 10/1997 | Barlow et al. |
| 5,692,898 A | 12/1997 | Orikasa et al. |
| 5,730,928 A | 3/1998 | Ghosh et al. |
| 5,773,099 A | 6/1998 | Tanaka et al. |
| RE35,863 E | 7/1998 | Sachdeva et al. |
| 5,800,162 A | 9/1998 | Shimodaira et al. |
| 5,803,728 A | 9/1998 | Orikasa et al. |
| 5,829,973 A | 11/1998 | Andreiko et al. |
| 5,910,273 A | 6/1999 | Thiel et al. |
| 5,911,102 A | 6/1999 | Takahashi et al. |
| 5,944,517 A | 8/1999 | Binder |
| 5,948,342 A | 9/1999 | Nakazawa et al. |
| 5,950,063 A | 9/1999 | Hens et al. |
| 5,972,269 A | 10/1999 | Barros et al. |
| 6,027,686 A | 2/2000 | Takahashi et al. |
| 6,048,954 A | 4/2000 | Barlow et al. |
| 6,059,949 A | 5/2000 | Gal-Or et al. |
| 6,071,117 A | 6/2000 | Andreiko et al. |
| 6,095,809 A | 8/2000 | Kelly et al. |
| 6,155,331 A | 12/2000 | Langer et al. |
| 6,183,515 B1 | 2/2001 | Barlow et al. |
| 6,244,870 B1 | 6/2001 | Sakata et al. |
| 6,276,930 B1 | 8/2001 | Pozzi |
| 6,354,836 B1 | 3/2002 | Panzera et al. |
| 6,391,251 B1 | 5/2002 | Keicher et al. |
| 6,444,167 B1 | 9/2002 | Shimodaira et al. |
| 6,495,073 B2 | 12/2002 | Bodenmiller et al. |
| 6,495,794 B2 | 12/2002 | Shi |
| 6,521,004 B1 | 2/2003 | Culler et al. |
| 6,531,678 B2 | 3/2003 | Yamamoto |
| 6,537,487 B1 | 3/2003 | Kuhns |
| 6,540,784 B2 | 4/2003 | Barlow et al. |
| 6,607,386 B1 | 8/2003 | Andersson et al. |
| 6,620,214 B2 | 9/2003 | McArdle et al. |
| 6,627,835 B1 | 9/2003 | Chung et al. |
| 6,638,886 B1 | 10/2003 | Gupta et al. |
| 6,676,895 B2 | 1/2004 | Kuhns |
| 6,710,290 B2 | 3/2004 | Yamamoto |
| 6,733,703 B2 | 5/2004 | Billiet et al. |
| 6,739,959 B2 | 5/2004 | Bodenmiller et al. |
| 6,744,618 B2 | 6/2004 | Divakar et al. |
| 6,811,744 B2 | 11/2004 | Keicher et al. |
| 6,814,926 B2 | 11/2004 | Geving et al. |
| 6,827,988 B2 | 12/2004 | Krause et al. |
| 6,846,862 B2 | 1/2005 | Schofalvi et al. |
| 6,878,456 B2 | 4/2005 | Castro et al. |
| 6,881,483 B2 | 4/2005 | McArdle et al. |
| 6,974,323 B2 | 12/2005 | Weigl et al. |
| 6,984,261 B2 | 1/2006 | Cummings et al. |
| 6,988,889 B2 | 1/2006 | Abels et al. |
| 6,994,549 B2 | 2/2006 | Brodkin et al. |
| 7,011,522 B2 | 3/2006 | Panzera et al. |
| 7,022,173 B2 | 4/2006 | Cummings et al. |
| 7,045,237 B2 | 5/2006 | Sridhar et al. |
| 7,063,813 B1 | 6/2006 | Nagaya et al. |
| 7,086,151 B2 | 8/2006 | Scancarello |
| 7,125,248 B2 | 10/2006 | Phan et al. |
| 7,140,113 B2 | 11/2006 | King et al. |
| 7,162,321 B2 | 1/2007 | Luthardt et al. |
| 7,236,842 B2 | 6/2007 | Kopelman et al. |
| 7,563,608 B2 | 7/2009 | Ishikawa et al. |
| 2001/0043452 A1 | 11/2001 | Divakar et al. |
| 2002/0033548 A1 | 3/2002 | Brodkin et al. |
| 2002/0131886 A1 | 9/2002 | Kuhns |
| 2002/0187065 A1 | 12/2002 | Amaya et al. |
| 2002/0187458 A1 | 12/2002 | Dolabdjian et al. |
| 2003/0001313 A1 | 1/2003 | Krause et al. |
| 2003/0069638 A1 | 4/2003 | Barlow et al. |
| 2003/0220424 A1 | 11/2003 | Schofalvi et al. |
| 2004/0011453 A1 | 1/2004 | Roosen et al. |
| 2004/0048223 A1 | 3/2004 | Phan et al. |
| 2004/0081573 A1 | 4/2004 | Newell |
| 2004/0106087 A1 | 6/2004 | Weigl et al. |
| 2004/0113301 A1 | 6/2004 | Burger et al. |
| 2004/0118158 A1 | 6/2004 | Schwertfeger et al. |
| 2004/0119180 A1 | 6/2004 | Frank et al. |
| 2004/0146423 A1 | 7/2004 | Scancarello |
| 2004/0152034 A1 | 8/2004 | Cummings et al. |
| 2004/0163262 A1 | 8/2004 | King et al. |
| 2004/0168610 A1 | 9/2004 | Conrad et al. |
| 2004/0182202 A1 | 9/2004 | Geving et al. |
| 2004/0226405 A1 | 11/2004 | Geving et al. |
| 2004/0234407 A1 | 11/2004 | Szabo et al. |
| 2005/0023710 A1 | 2/2005 | Brodkin et al. |
| 2005/0056350 A1 | 3/2005 | Dolabdjian et al. |
| 2005/0109060 A1 | 5/2005 | Cummings et al. |
| 2005/0133527 A1 | 6/2005 | Dullea et al. |
| 2005/0136176 A1 | 6/2005 | Rosenflanz et al. |
| 2005/0196312 A1 | 9/2005 | Nyberg et al. |
| 2005/0244782 A1 | 11/2005 | Chishti et al. |
| 2005/0261795 A1 | 11/2005 | Ghosh et al. |
| 2006/0003095 A1 | 1/2006 | Bullen et al. |
| 2006/0122719 A1 | 6/2006 | Kopelman et al. |
| 2006/0150406 A1 | 7/2006 | Scancarello |
| 2006/0166159 A1 | 7/2006 | Abels et al. |
| 2006/0168815 A1 | 8/2006 | Saliger et al. |
| 2006/0185170 A1 | 8/2006 | Lewis et al. |
| 2006/0210781 A1 | 9/2006 | Nagaya et al. |
| 2006/0246397 A1 | 11/2006 | Wolf |
| 2007/0065329 A1 | 3/2007 | Nyberg et al. |
| 2007/0068340 A1 | 3/2007 | Nyberg et al. |
| 2007/0142206 A1 | 6/2007 | Binder et al. |
| 2007/0157475 A1 | 7/2007 | King et al. |
| 2007/0160949 A1 | 7/2007 | Voudouris |
| 2007/0233299 A1 | 10/2007 | Kopelman et al. |
| 2007/0264606 A1 | 11/2007 | Muha et al. |
| 2008/0057475 A1 | 3/2008 | Feith |
| 2008/0070182 A1 | 3/2008 | Wyllie et al. |
| 2008/0213718 A1 | 9/2008 | Abels et al. |
| 2009/0017411 A1 | 1/2009 | Pospisil et al. |

FOREIGN PATENT DOCUMENTS

| | | |
|---|---|---|
| EP | 0776638 A2 | 6/1997 |
| EP | 1033193 A1 | 9/2000 |
| EP | 1077099 A2 | 2/2001 |
| EP | 1125679 A2 | 8/2001 |
| JP | 06108112 A | 4/1994 |

(56) References Cited

FOREIGN PATENT DOCUMENTS

| JP | 06212206 A | 8/1994 |
|---|---|---|
| JP | 07106192 A | 4/1995 |
| JP | 07126712 A | 5/1995 |
| JP | 2002274950 A | 9/2002 |
| JP | 2003027106 A | 1/2003 |
| JP | 2003-286507 A | 10/2003 |
| JP | 2004174917 A | 6/2004 |

OTHER PUBLICATIONS

Kamran Imen et al., Pulse CO2 Laser Drilling of Green Alumina Ceramic, IEEE Transactions on Advanced Packaging, vol. 22, No. 4, pp. 620-623, Nov. 1999.

J.A. Todd et al., 3-D Laser Shaping of Ceramic and Ceramic Composite Materials; Solid Freeform Fabrication Proceedings, pp. 305-313, 1995.

U.S. Patent and Trademark Office, Office Action in U.S. Appl. No. 11/042,025, Oct. 5, 2007.

U.S. Patent and Trademark Office, Final Office Action in U.S. Appl. No. 11/193,239, Jan. 8, 2009.

U.S. Patent and Trademark Office, Non-Final Office Action in U.S. Appl. No. 12/104,958, Apr. 20, 2010.

U.S. Patent and Trademark Office, Final Office Action in U.S. Appl. No. 11/193,571, Dec. 17, 2009.

U.S. Patent and Trademark Office, Non-Final Office Action in U.S. Appl. No. 11/193,571, Mar. 13, 2009.

European Patent Office, European Examination Report in EP Application No. 06700916.7, Jul. 6, 2009.

U.S. Patent and Trademark Office, Non-final Office Action issued in U.S. Appl. No. 11/193,239, Nov. 1, 2007.

U.S. Patent and Trademark Office, Non-final Office Action issued in U.S. Appl. No. 11/193,239, Jul. 2, 2008.

U.S. Patent and Trademark Office, Non-final Office Action issued in U.S. Appl. No. 11/193,239, Feb. 12, 2010.

U.S. Patent and Trademark Office, Final Office Action issued in U.S. Appl. No. 12/104,958, Aug. 5, 2010.

Mexican Patent Office, Office Action in Mexican Patent Application No. Mx/a/2007/008763 dated Mar. 22, 2012.

Japanese Patent Office, Office Action in Japanese Patent Application No. 2007-551594 dated Mar. 27, 2012.

U.S. Patent and Trademark Office, Office Action in U.S. Appl. No. 11/193,571 dated Apr. 28, 2011.

U.S. Patent and Trademark Office, Office Action in U.S. Appl. No. 11/193,571 dated Jan. 6, 2012.

U.S. Patent and Trademark Office, Office Action in U.S. Appl. No. 12/398,624 dated May 4, 2011.

Chinese Trademark Office, Office Action in Chinese Patent Application No. 200680001291.X dated Dec. 20, 2011.

Mexican Patent Office, Office Action in Mexican Patent Application No. Mx/a/20071008763, dated Nov. 9, 2012.

Korean Patent Office, Office Action in Korean Patent Application No. 10-2007-7015465, dated Oct. 31, 2012.

European Patent Office, Intent to Grant in European Patent Application No. EP06700916, dated Sep. 24, 2012.

Japanese Patent Office, Office Action in Japanese Patent Appliation No. 2007-551594, dated Dec. 10, 2012.

Korean Patent Office, Office Action in Korean Patent Application No. 10-2007-7015465, dated Jun. 26, 2013.

U.S. Patent and Trademark Office, Office Action in U.S. Appl. No. 12/398,624 dated Dec. 13, 2013.

U.S. Patent and Trademark Office, Patent Trial and Appeal Board Decision on Appeal in U.S. Appl. No. 12/398,624 dated Sep. 24, 2013.

METHOD OF MANUFACTURING AN ORTHODONTIC BRACKET HAVING A LASER SHAPED GREEN BODY

CROSS-REFERENCE TO RELATED APPLICATIONS

This application is a continuation of U.S. application Ser. No. 13/936,589, which is filed Jul. 8, 2013, which is a continuation of U.S. Pat. No. 8,479,393, filed Nov. 5, 2010, which is a continuation of U.S. application Ser. No. 12/104,958, filed Apr. 17, 2008, abandoned, which is a division of U.S. application Ser. No. 11/193,239, filed Jul. 29, 2005, abandoned, which is a continuation-in-part of U.S. application Ser. No. 11/042,025, filed Jan. 25, 2005, abandoned, each of which is incorporated by reference herein in its entirety.

BACKGROUND OF THE INVENTION

1. The Field of the Invention

The present invention relates to orthodontic brackets. More particularly, the present invention relates to cutting and shaping an orthodontic bracket shaped green metal body with a laser prior to sintering.

2. The Relevant Technology

Orthodontic brackets have been used extensively for correcting dental malformations such as crooked teeth or large gaps between teeth. The treatment can involve applying force to the teeth in order to move the teeth into a correct alignment. The brackets are configured to provide a force to the teeth in the arch that are being aligned. As such, each bracket has a bonding surface that is configured to be affixed to a tooth. Accordingly, a bond is formed between the bonding surface and the tooth that can withstand the forces required to properly align the teeth for the duration of the treatment.

Various types of materials have been used to make orthodontic brackets, including metals, polymers, and composites. Metals are commonly used for the brackets because of their strength and their ability to be fabricated into many different shapes. Accordingly, brackets can be formed by molding and sintering metal particles, or by milling a metal piece into the shape of a base plate. A common method of producing an orthodontic bracket can include forming a green metal body in a mold, and sintering the green metal body into a finished part. Additionally, a new mold may have to be created for each orthodontic bracket configured to fit on each tooth because a universal bracket design may be impracticable to provide sufficient bonding with different shaped teeth. For example, a universal bonding surface curvature may not provide adequate bonding for all teeth because the lingual and/or buccal surfaces often vary in curvature between different types of teeth as well as between people.

Typically, an adhesive is used to form a chemical bond between the bonding surface of the bracket and the tooth. The chemical bond between the bonding surface and the tooth can be weak and subject to failure because of the physical properties of the bonding surface. Additionally, a smooth bonding surface, which is an unfavorable characteristic in terms of bonding, can increase the chance of the bond failing. However, improvements in dental bonding techniques have resulted in the bonding surface to be fabricated to include recesses or undercuts. These recesses or undercuts in the bonding surface can increase the bond strength between the dental bracket and the tooth because the adhesive can fill into these physical formations and harden in order to provide a mechanical aspect to the bond.

In order to provide recesses into the bonding surface a mold can be configured to include raised portions, recessed portions, or irregularities in the base surface. Alternatively, a bracket that is hardened by sintering can be cut or shaped to include recesses or undercuts. This can be performed by cutting into the hardened metal bonding surface with a laser or other milling apparatus. As such, cutting and milling a sintered piece with a laser can result in a decrease in the biocompatibility of the bracket because the cut piece will be charred or blackened as is characteristic of being cut with a laser. Also, any cutting or milling of a bracket that has been sintered can decrease its biocompatibility because the oxidized external surface that results from sintering will be destroyed.

Although a bracket bonding surface having recesses or undercuts can be produced, there are drawbacks to the current processes. The size limitations of the base result in extremely small recesses, undercuts, or overhangs, which can be exceedingly difficult to form by merely using a mold. On the other hand, milling or cutting a hardened sintered metal can require durable cutting machinery or a laser that is strong enough to cut into the hardened metal in order to form recesses or overhangs. However, improper milling or cutting can create fissures or otherwise ruin an orthodontic bracket that is nearly finished. Additionally, milling or shaping a hardened metal can waste valuable materials that have already been solidified into a finished and usable state.

Therefore, what is needed is an improved process for producing and shaping an orthodontic bracket that does not cut or mill hardened metal. In addition, an improved process is needed that produces a base surface with recesses and overhangs.

BRIEF SUMMARY OF EMBODIMENTS OF THE INVENTION

Generally, an embodiment of the present invention provides for a green metal body having a shape of an orthodontic bracket, which can be used during a process for making an orthodontic bracket. Alternatively the green metal body can have the shape of an orthodontic bracket base plate. As such, a green metal body includes a plurality of metal particles and a binder in an amount and disposition within the plurality of metal particles sufficient to hold the metal particles together prior to sintering to form a usable bracket. The metal particles are held together sufficiently to define an exterior surface in substantially the shape of an orthodontic bracket and/or orthodontic bracket base plate.

Additionally, the exterior surface includes at least one laser-cut portion that has a topology characterized by a plurality of recesses and/or elevations comprising metal particles. Such recesses and/or elevations remain after sintering to yield a final bracket and assist in bonding the bracket to a person's teeth through, e.g., mechanical interlocking of an adhesive in and around the recesses and/or elevations as well as increased surface area. Other portions of the green metal body (e.g., archwire slot, tie wings, etc.) may be formed by laser shaping. In some embodiments, at least a portion of the metal particles disposed at or near the green body surface may be fused together prior to sintering.

In many cases, the metal particles removed by laser-shaping are not re-deposited onto the surface of the green metal body but are removed and discarded. Whether or not the metal particles are re-deposited largely depends on the relationship between the temperature at which the organic binder melts, burns or decomposes and the temperature at which the metal particles melt or become vaporized. The higher the temperature differential, the greater the likelihood that the laser will melt, burn or decompose the binder without actually melting or vaporizing the metal particles. In addition, one of skill in the art can, in light of the teachings contained herein, select a laser and/or cutting procedure that ensures clean removal of metal particles in order to prevent their being re-deposited on the green metal body surface.

One embodiment of the present invention provides a method of making a green metal body. The method can include introducing (e.g., injecting) metal particles into a mold, and introducing (e.g., injecting) a binder into the mold in an amount sufficient to hold the metal particles together. The metal particles and the binder are formed into a green metal body, where the metal particles and binder can be shaped into a green metal body in substantially the shape of an orthodontic bracket and/or a base plate. Alternatively, the green metal body can be pressed into a form that can be further shaped into the shape of an orthodontic bracket.

Additionally, the green metal body is shaped with a laser by cutting the exterior surface to form any of the features of an orthodontic bracket and/or base plate. Also, the green metal body, or more particularly, a surface thereof in the shape of a bonding surface can have a plurality of elevations, recesses and/or undercuts formed thereon with the laser.

Another embodiment of the present invention provides for making an orthodontic bracket and/or base plate from a laser-modified green metal body. Accordingly, the green metal body can be processed into an orthodontic bracket and/or base plate by sintering the laser-modified green metal body into a sintered metal body. The exterior surface of the sintered metal body defines the shape of an orthodontic bracket, and can include at least one laser-cut portion thereon. The laser-cut portion is formed by cutting the green metal body with a laser before being sintered. This can cause the laser-cut portion of the sintered metal body to be substantially devoid of charring as commonly occurs when a sintered metal body is cut with a laser. Also, the laser-cut portion can be a recess (e.g., an undercut) formed into the exterior surface, or more particularly, formed into a bonding surface on the orthodontic bracket and/or base plate.

Regardless of the fact that the green metal body is substantially in the shape of the finished sintered bracket, the green metal body is typically about 15-30% larger than the finished bracket and is therefore not itself an orthodontic bracket. In addition to being oversized, the green metal body lacks sufficient strength to handle the strong torquing forces to which an actual bracket is subjected to during an orthodontic treatment (e.g., as a result of an archwire bearing down on the bracket within the archwire slot in order to reposition the patient's tooth during treatment). When the green metal body is sintered it shrinks to the size of an orthodontic bracket and obtains sufficient strength to function as an orthodontic bracket.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF EMBODIMENTS OF THE INVENTION

Embodiments of the present include orthodontic brackets, green metal bodies, and associated methods of making or using the brackets or green metal bodies. More particularly, embodiments of the present invention include green metal bodies that are laser-modified into the shape of an orthodontic bracket that can be sintered into a functional orthodontic bracket. It should be understood that terminology employed herein is used for the purpose of describing particular embodiments only and is not intended to be limiting.

Figure 1:
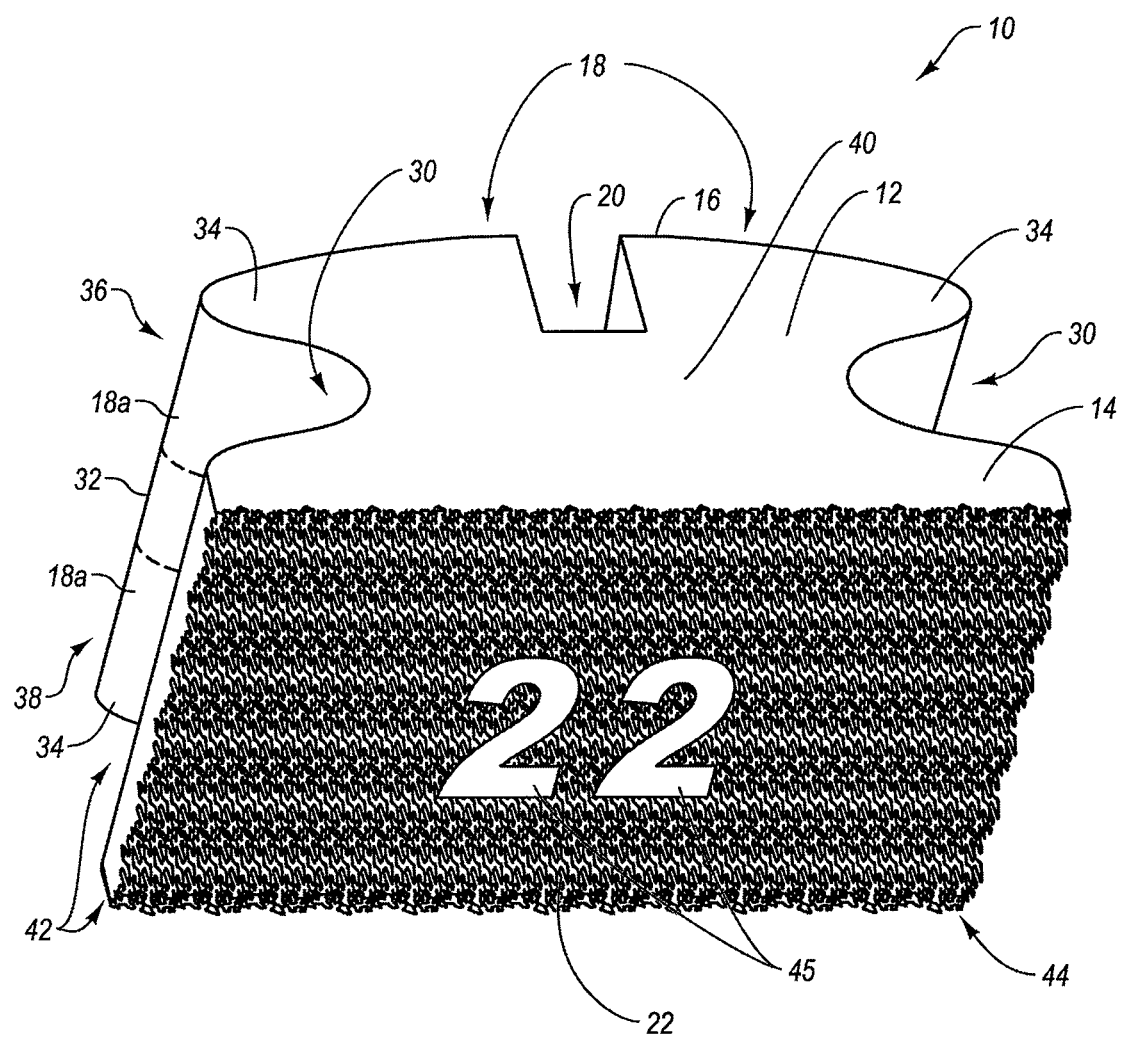
FIG. 1 is a perspective view illustrating an exemplary orthodontic bracket formed according to the invention.

FIG. 1 depicts an embodiment of an orthodontic bracket 10 in accordance with the present invention. The orthodontic bracket 10 includes a body 12 and a base plate 14 integrated in a continuous piece. The orthodontic bracket 10 also includes an external surface 16 that defines the shape of the bracket 10. The body 12 includes at least one tie wing 18 and an archwire slot 20 that is open to the upper side of the body 12. The base plate 14 includes a bonding surface 22 having a rough topology 44 including a plurality of protrusions, recesses, and/or undercuts. Additionally, the bonding surface 22 can be configured to be the negative shape of a lingual or buccal side of a tooth so as to fit thereon.

The body 12 can be configured into a ligature-requiring bracket for use with a ligature or fastener to secure an archwire to the bracket 10. The ligature can be essential to ensure that the tensioned archwire is properly positioned around the dental arch, and to prevent the wire from being dislodged from the bracket 10 during eating, teeth brushing, and other daily activities as well as the force required to move and align the teeth. For example, the ligature can be a small elastomeric O-ring, which is stretched around the archwire and secured to the body 12. Metal ligatures can also be used and are well known in the art.

In order to retain a ligature, the body 12 of each bracket can include tie wings 18, or a pair of tie wings 18a. The tie wings 18 can include at least one lobe 34 that protrudes from the body 12. As such, the tie wings 18 can be configured to be couplable with ligatures by having each lobe 34 curve into a ligature groove 30. The ligature groove 30 can be continuous with the external surface 16, where the external surface 16 curves around the lobe 34 and in towards the center of the body 12. When the body 12 includes a pair of tie wings 18a, a lobe spacer 32 defined by the exterior surface 16 can separate the tie wings 18 into tie wing pairs 18a. More particularly, the lobe spacer 32 can be a slot or gap that separates the lobes 34 on the mesial side 36 of the body 12 from the distal side 38 of the body 12.

The archwire slot 20 is configured to retain an archwire therein. As such, the archwire slot 20 traverses the length of the body 12 from the mesial end 40 to the distal end 42. The archwire slot 20 can be squared (as depicted in FIG. 1) or rounded to accommodate archwires having squared or rounded cross-sectional areas. Alternatively, other archwire slot 20 shapes can be formed into the bracket 10. Also the depth and/or width of the archwire slot 20 can be varied.

In an alternative embodiment, the orthodontic bracket can be configured into a self-ligating bracket (not shown). Self-ligating brackets can be a single piece that includes a ligation cover integrated with the body so that the ligation cover can be closed over the archwire and secure the archwire to the bracket. The ligation cover typically serves to replace the ligatures, and includes an attachment member that releasably couples with the body so as to contain the archwire therebetween.

Additionally, the bonding surface 22 on the base plate 14 is configured to have a topology 44 that includes a plurality of protrusions, recesses and/or undercuts (as shown in FIG. 2). The topology 44 is designed to enhance the bonding with a tooth. Accordingly, the protrusions, recesses, and/or undercuts of the topology 44 can either independently or together serve to increase the surface area of the bonding surface 22 for a bonding agent to be applied thereto. In various embodiments, the topology 44 can have rounded features to reduce friction points, and/or the protrusions, recesses and/or undercuts can be spaced close together or spread out across the bonding surface 22. Also, features in the topology can be uniformly arranged or randomly distributed. The bonding agent can encompass the protrusions and penetrate into the recesses and/or the undercuts to impart a mechanical aspect to the bonding between the bonding surface 22 and a tooth. This occurs when the bonding agent solidifies and interlocks the bracket 10 to the tooth.

In one embodiment, each orthodontic bracket 10 can be shaped to fit on a particular type of tooth, or a particular tooth in a person's mouth. Accordingly, the bonding surface 22 can be shaped to have a curvature that mates with the tooth it is adhered to. In order to identify which tooth the bonding surface 22 mates with, the bonding surface 22 can include identification indicia 45 carved therein. The identification indicia 45 can notify a dental professional to which tooth the particular bracket applies, where the identification indicia 45 can include the Universal Numbering System, Palmer Notation, and FDI-Two Digit Notation. For example, a bonding surface 22 that includes the number "22" uses the FDI-Two Digit Notation and identifies the upper left lateral incisor. As depicted, the identification indicia can either be carved into the base as a recess, protrusion, or formed by undercuts, recesses and protrusions.

In another embodiment, a three-dimensional model of the patient's teeth can be used to form the shape of the bonding surface 22. The three-dimensional model of a tooth can be ascertained and input into a computer. The computer can then determine the correct shape of the bonding surface 22 of each bracket for a specific tooth. Also, the computer can generate other features and positioning to be included on the bracket 10. Accordingly, the base can be shaped according to the computer specifications, as well as signing angulations and slot positions.

Figure 2A:
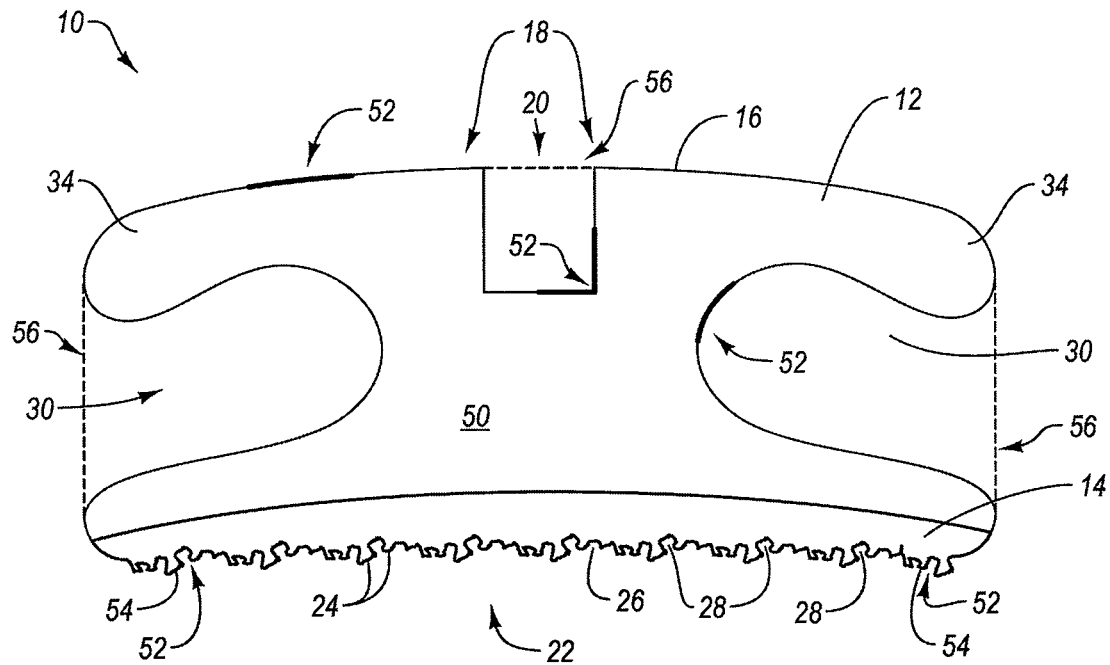
FIG. 2A is a side view illustrating an exemplary green metal body in the shape of an orthodontic bracket.
Figure 2B:
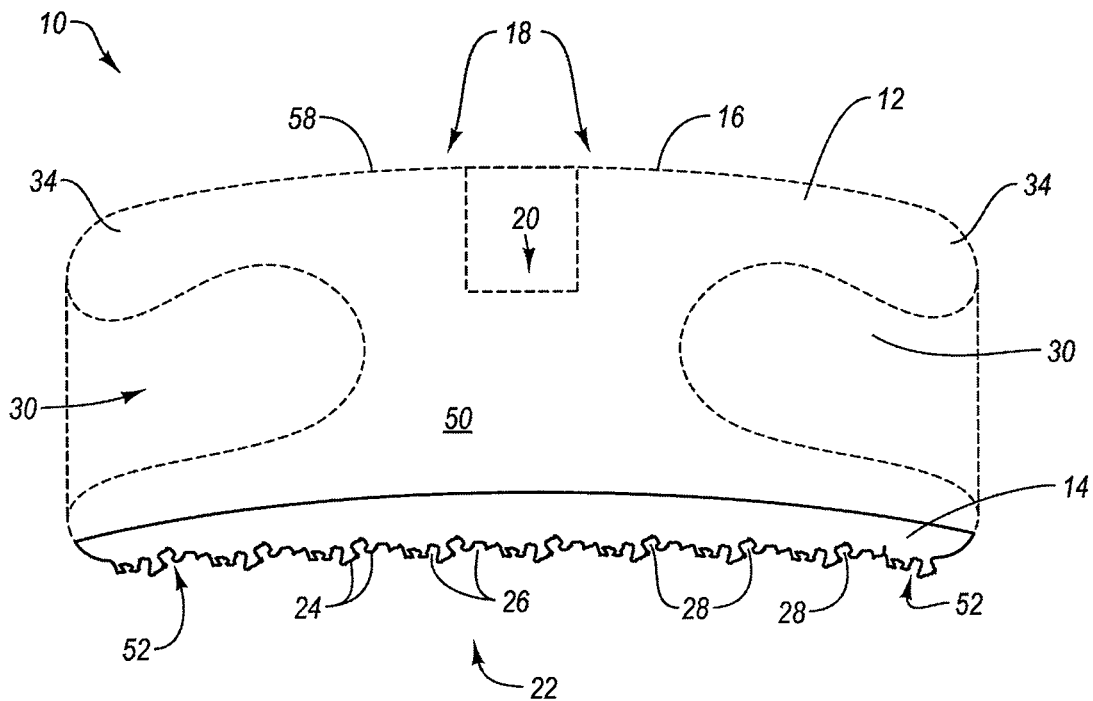
FIG. 2B is a side view illustrating an exemplary green metal body in the shape of an orthodontic bracket base plate.

FIGS. 2A and 2B depict alternative embodiments of green metal bodies 50 in accordance with the present invention. FIG. 2A depicts a green metal body 50 in the shape of an orthodontic bracket 10, and FIG. 2B depicts a green metal body 50 in the shape of a base plate that can be further processed into the shape of an orthodontic bracket 10 as shown. The green metal body 50 can include a body 12 and a base plate 14 cooperatively in the shape of an orthodontic bracket 10 defined by an external surface 16. The body 12 includes tie wings 18 and an archwire slot 20 that is open to the upper side of the body 12. The tie wings 18 each include a lobe 34 that is adjacent to a lobe recess 30. The base 14 includes a bonding surface 22 comprised of a plurality of protrusions 24, recesses, 26 and/or undercuts 28. The structure referred to as "bonding surface 22" of green metal body 50 is not an actual "bonding surface" because the green metal body 50 is not suitable for use as a bracket prior to sintering to form a final sintered bracket but is merely a precursor thereto.

The green metal body 50 has the shape of an orthodontic bracket, and can be used to make an orthodontic bracket by sintering the green metal body 50. As used herein, the terms "shape," "form" or other similar terms are used to identify the appearance of an object, and it is not intended to strictly construe the dimensions or proportions of the object. For example, while the green metal body 50 is in the shape of an orthodontic bracket, this should be construed to include the precise dimensions required to properly fit on a tooth as well as the larger dimensions of a green metal body that will shrink during sintering. As such, a green metal body 50 in the shape of an orthodontic bracket can be larger than a finished sintered bracket that is ready to be affixed to a tooth.

The green metal body 50 includes a plurality of metal particles. The metal particles can be selected from aluminum, nickel, titanium, copper, cobalt, stainless steel, and the like as well as various alloys thereof. The metal particles can be comprised of, for example, a nickel-titanium alloy powder. Alternatively, the particles can be comprised of a mixture of ceramic and metal. More particularly, it is preferable that the metal particles be comprised of a metal that can be pulverized and sintered. For example, if stainless steel brackets are desired, a pre-alloyed fine-grained stainless steel powder can be used. The characteristics of the powder can depend on the structure of the planned green metal body as well as the finished orthodontic bracket. In part, the size of the bracket can determine the size of the metal particles, where smaller brackets may need smaller particles. For example, the average diameter of the metal particles can range from about 0.001 to about 1 mm.

The green metal body 50 also includes a binder in an amount and disposition within the plurality of metal particles sufficient to hold the metal particles together. The binder can be a thermoplastic made of at least one organic material. Examples of organic binders that can be used to bind metal particles together in accordance with the present invention include various polymers, polyolefins, silicones, acrylics, latexes, waxes, oils, greases, plasticizers, lignosulfonates, polysaccharides, celluloses and derivatives thereof, starches and derivatives thereof, other natural polymers (e.g., proteins), natural and synthetic rubbers, and the like. More specific examples of polymeric binders can include polypropylenes, polyethylenes, acrylic polymers, polystyrenes, polyethylene-vinyl acetate, polyethylene vinyl alcohol, polyethylene acetate, chlorinated polyethylenes, polyisoprenes, polybutadienes, styrene-butadiene di- and tri-block polymers, polychloroprenes, polyethylene-propylenes, chlorosulfonated polyethylenes, polyurethanes, styrene isoprene polymers, styrene ethylbutylene polymers, styrene butadiene rubber latex, polychloroprene latex, polymethylmethacrylate, polyethylmethacrylate, polydimethylsiloxanes, and the like. It should be recognized that many other types of organic binders can be used in order to bind the metal particles into green body compositions for processing in accordance with the present invention.

The ratio of metal particles and binder can vary depending on the particle sizes and the type of binder as well as on other factors. For example, the metal to binder weight ratio can range from about 70:30 to about 98:2. Additionally, the weight ratio can range from about 75:25 to about 95:5. It is to be understood that such a range format is used merely for convenience and brevity and should be interpreted flexibly to include not only the numerical values explicitly recited as the limits of the ranges, but also to include all the individual numerical values or sub-ranges encompassed within that range as if each numerical value and sub-range is explicitly recited. For example, the metal-binder weight ratio of about 70:30 to about 98:2 should be interpreted to include not only the explicitly recited limits of about 70:30 and about 98:2, but also to include such individual ratios such as 75:25, 80:20, 85:15, as well as sub-ranges between these individual ratios. Also, it should be recognized that any metal binder ratio within the described increments can be used as long as green metal body is sufficiently held together to be handled and shaped with a laser in accordance with the present invention.

With continuing reference to FIGS. 2A and 2B, the green metal body 50 can include at least one laser-cut portion 52 on the exterior surface 16. The exterior surface 16 is intended to be any surface on the exterior of the green metal body 50. As such, the exterior surface 16 can include at least one laser-cut portion 52 having a topology 44 characterized by a plurality of irregular elevations formed by the metal particles. Alternatively, the irregular elevations can be in the size range to be either macroscopically visible or microscopically visible. As used herein, the term "macroscopic" can include features that are visible with the naked eye. For example, the macroscopic irregular elevations can be easily seen with the naked eye without any magnification. Alternatively, the term "microscopic" as used herein refers to the need for magnification to be used in order to visualize the irregular elevations.

In one embodiment, the green metal body 50 can have a laser-cut portion 52 on the external surface 16. The laser-cut portion 52 is cut into the green metal body 50 so that a significant amount of green material is removed in order to form the orthodontic bracket shaped piece. Accordingly, the green metal body 50 can initially have a rectangular cross-sectional area as shown with the dashed-lines 56. As such, the laser-cut portion 52 can include the external surface 16 that is formed by cutting the green metal body 50 into the shape of the orthodontic bracket as shown. Alternatively, the green metal body 50 can be cut in to the shape of a self-ligating orthodontic bracket (not shown). Thus, a minor portion or a significant portion of the external surface 16 can be included within the laser-cut portion.

In another embodiment, the laser-cut portion 52 can include a plurality of protrusions 24, recesses, 26 and/or undercuts 28. As such, the exterior surface 16 can include a plurality of protrusions 24, recesses 26, and/or undercuts 28, each having a topology 44 formed by the metal particles. In some cases, at least a portion of the metal particles disposed on the protrusions 24, recesses 26, and/or undercuts 28 or topology 44 may be at least partially fused or melted together. Whether this occurs depends on whether the metal particles are heated to a high enough temperature before being removed or ejected from the green metal body as a result of locally melting, burning or decomposing the organic binder that holds the metal particles together.

FIG. 2B depicts an orthodontic bracket base plate 14 that can be integrated with a body 12 to form an orthodontic bracket 10 (shown by the dashed-lines 58). Accordingly, the base plate 14 can also include at least one laser-cut portion 52 and/or a plurality of protrusions 24, recesses 26, and/or undercuts 28. Additionally, the bonding surface 22 or other laser-cut portion 52 can have a topology 44 formed by metal particles, in some cases, where a portion of the particles may be melted or fused together.

The green metal body 50 in the shape of the base plate 14 can later be integrated with the body 12 before or after being sintered. The body 12 can be comprised of metal, ceramics, or plastics. For example, a green metal body 50 in the shape of the base plate 14 can be formed and sintered prior to being molded with a ceramic or plastic to form the shape of an orthodontic bracket is depicted by the dashed-line 58.

Figure 3A:
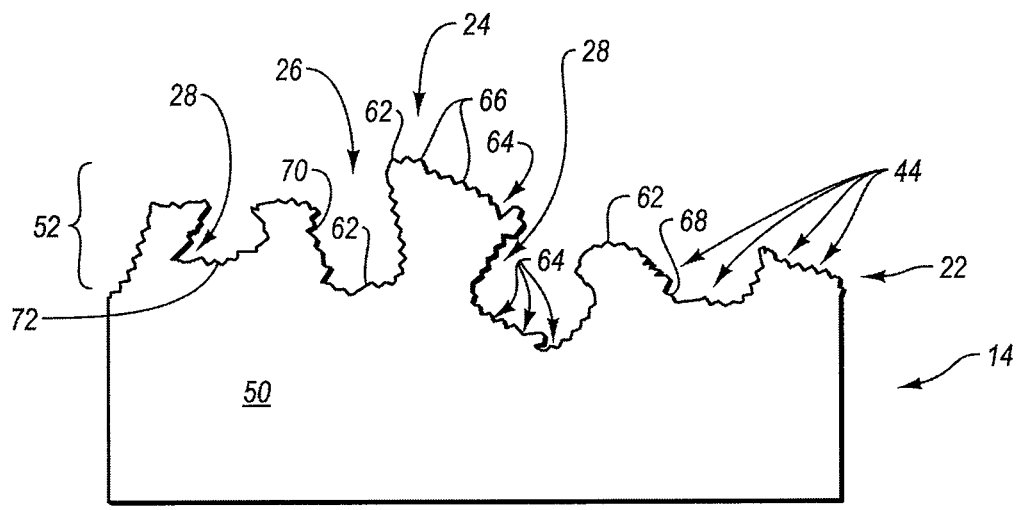
FIGS. 3A-3C are side views illustrating exemplary embodiments of green metal bodies forming a portion of a bonding surface of an orthodontic bracket.

FIG. 3A depicts an embodiment of a green metal body 50 having a laser-cut portion 52 in accordance with the present invention. The laser-cut portion 52 includes a topology 44 that defines the exterior surface of the laser-cut portion 52. In one embodiment, the laser-cut portion 52 can be on the bonding surface 22. The topology 44 includes a plurality of macroscopic or larger irregular elevations 62 which can be protrusions 24, recesses 26, and/or undercuts 28. The larger irregular elevations 62 can also include microscopic or smaller irregular elevations 64, which can also be micro-protrusions 66, micro-recesses 68, and micro-undercuts 70.

The larger irregular elevations 62 as well as smaller irregular elevations 64 can be comprised of a plurality of metal particles and a binder holding the metal particles together to form the green metal body 50. In one embodiment, a portion of the metal particles on the topology 44 are melted together to form a melted surface layer. In another embodiment, the metal particles on the topology 44 are adhered together with the binder. In yet another embodiment, a portion of the topology 44 of the green metal body 50 includes a charred layer or blackened layer. The charred layer or blackened layer can be characterized by surface features that result from the vaporizing, melting, and/or burning that accompany the process of cutting the green metal body 50 with a laser.

When the laser-cut portion forms protrusions 24, recesses 26, and/or undercuts 28 into the bonding surface 22, the strength of the bond formed between the orthodontic bracket and the tooth can increase. This is because the bonding material or adhesive can encapsulate around the protrusions 24 and penetrate into the recesses 26 and undercuts 28. This interaction between the bonding surface 22 and the adhesive can provide a mechanical aspect to the bond when the adhesive hardens and interlocks with the topology 44. While this can occur with the larger or macroscopic irregular elevations 62, the mechanical bond can be enhanced when the laser-cut portion 52 also includes the smaller or microscopic irregular elevations 64 comprised of micro-protrusions 66, micro-recesses 68, and/or micro-undercuts 70. In another aspect, the microscopic irregular elevations 64 can increase the interfacial surface that is capable of coming into contact with the adhesive.

Figure 3B:
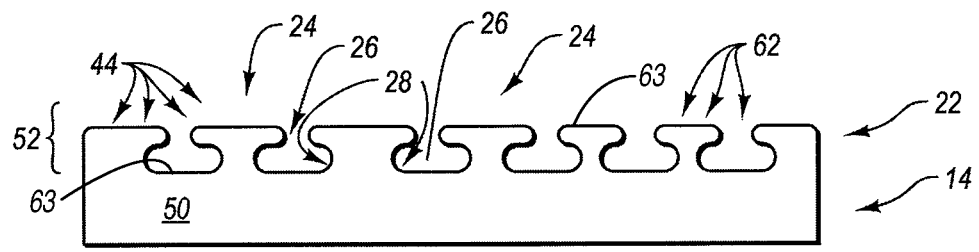

FIG. 3B depicts another embodiment of a green metal body 50 having a laser-cut portion 52 in accordance with the present invention. The laser-cut portion 52 includes a topology 44 that defines the exterior surface of the laser-cut portion 52, which can be on the bonding surface 22. The topology 44 includes a plurality of macroscopic or larger elevations 62 which can be protrusions 24, recesses 26, and/or undercuts 28. The larger elevations 62 can be cut into the green metal body 50 to be characterized by having a topology 44 that is substantially smooth so that the larger irregular elevations 62 have surfaces 63 that are substantially devoid of microscopic irregular elevations. Accordingly, the topology 44 of the laser-cut portion 52 on the green metal body 50 can be configured to range from being rough to smooth.

Without being bound to any particular methodology, it is thought that the smoother topology 44 depicted in FIG. 3B compared to the topology 44 of FIG. 3A can be obtained by using variations in the method of cutting the green metal body 50 with a laser. As such, the power of the laser, the atmosphere, and/or the orientation of the surface being laser-cut can be varied. Also, the composition of the green metal body can be varied to achieve topologies having varying degrees of smoothness or roughness.

Figure 3C:
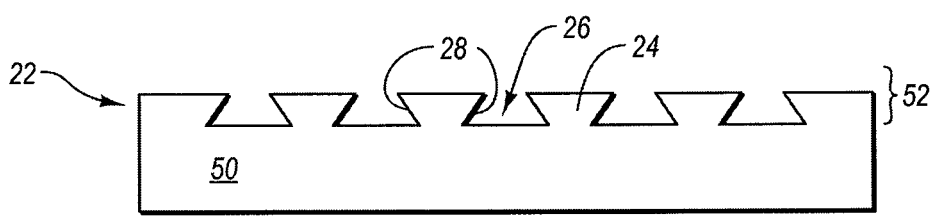

FIG. 3C depicts another embodiment of a green metal body 50 having a laser-cut portion 52 in accordance with the present invention. The laser-cut portion 52 includes a plurality of trapezoidal protrusions 24 formed by cutting trapezoidal recesses 26 therein to form undercuts 28 in the green metal body 50. The protrusions 24, recesses 26, and undercuts 28 yield a bonding surface 22 that increases the bond of the final sintered orthodontic bracket to a person's tooth.

In some embodiments, a smoother topology on a laser-cut portion can lend to laser-shaping a substantially rectangular green metal body into the shape of an orthodontic bracket. This is because the smoother topology on a green metal body can be even smoother to the touch after being sintered. As such, the sintered body can be smooth enough that the bracket may not have to undergo any post-sintering grinding or sanding to render a surface that has the proper characteristics for being placed into a mouth. As such, the tie wings, lobes, archwire slot, ligature grooves, self-ligating features, and other features can be carved into a green metal body with a laser.

Figure 4A:
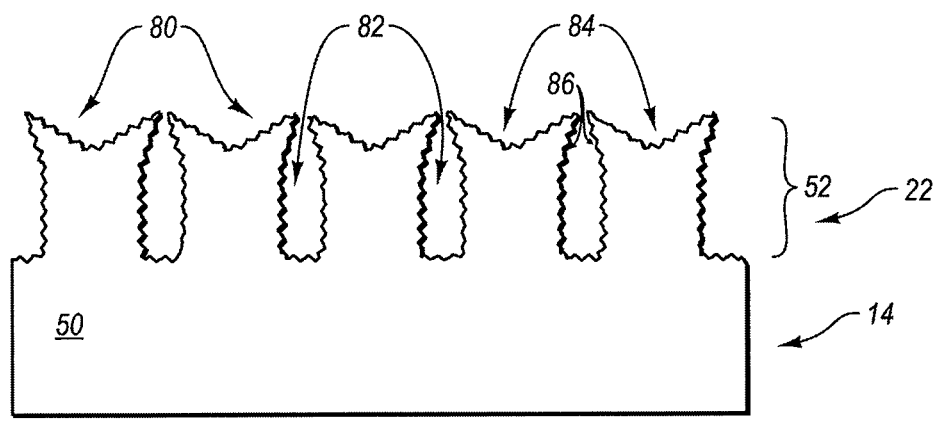
FIGS. 4A-4C are side views illustrating exemplary embodiments of green metal bodies forming a portion of a bonding surface of an orthodontic bracket.
Figure 4B:
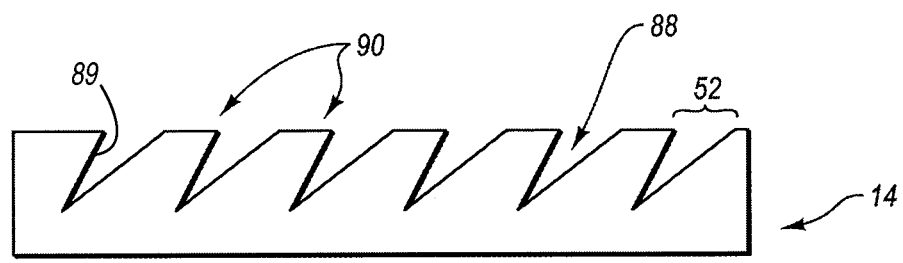
Figure 4C:
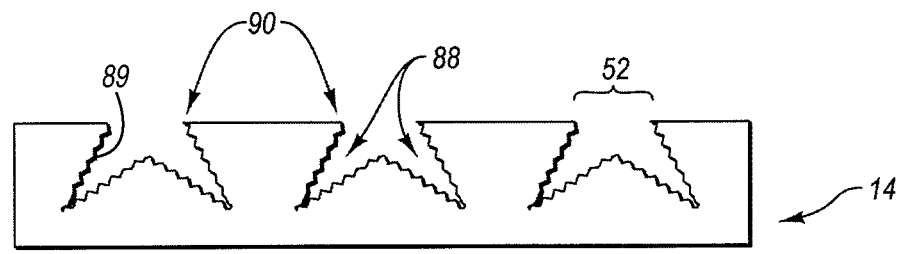

FIGS. 4A, 4B, and 4C depict various alternative examples, without limitation, of laser-cut portions 52 on the bonding surface 22 of a green metal body 50 having the shape of an orthodontic bracket (not shown) and/or a base 14. In FIG. 4A, the laser-cut portions 52 are comprised of long columnar protrusions 80 separated by deep recesses 82 defined by the surface of the laser cut portions 52. Additionally, the long columnar protrusions 80 can include smaller recesses 84 cut therein. Also, the long columnar protrusions 80 can be formed to include undercuts 86 to aid in mechanically bonding the orthodontic bracket to the tooth.

In alternative embodiments, FIGS. 4B and 4C depict a green metal body 50 base 14 having laser cut portions 52 cut into the bonding surface 22. The laser-cut portions 52 can remove portions of the green metal body 50 to provide for recesses 88, undercuts 89, and overhangs 90. The recesses 88, undercuts 89, and overhangs 90 can be wedge shaped slices cut into the bonding surface 22 to provide voids for receiving the bonding agent or adhesive when the bracket is affixed to the tooth. As depicted, the undercuts 89 can be formed by hitting the bonding surface with a laser at an angle, which also forms the overhangs 90.

Additionally, the green metal body can be cut with a laser to form the identification indicia that determines which tooth the bracket will be adhered to. Accordingly, the identification indicia can be formed by being a recess, a protrusion, or a plurality of irregular elevations. The identification indicia carved into the green metal body can include the Universal Numbering System, Palmer Notation, and FDI-Two Digit Notation.

In another embodiment, a three-dimensional model of the patient's teeth can be used to form the shape of the bonding surface 22 in the green metal body. The three-dimensional model can be ascertained and input into a computer. The computer can then determine the correct shape of the bonding surface 22 of the green metal body. Also, the computer can generate other features and positioning indicators to be carved into the green metal body. Accordingly, the green metal body can be shaped according to the computer specifications to include signing angulations and slot positions.

While certain features and configurations of the recesses, protrusions, and undercuts have been depicted and discussed, the present invention should not be construed to be limited thereto. Accordingly, the general features of the present invention could be applied to other configurations to provide increased surface areas for mechanically bonding the bracket to the tooth.

The present invention also provides for methods of making a green metal body having a shape of an orthodontic bracket and/or a base plate. As used herein, the methods described in making an orthodontic bracket can also be used for making a base plate. Accordingly, in the following discussion a method of making a base plate is intended to be included in the method for making the orthodontic bracket. An embodiment of such a method can include introducing (e.g., injecting) metal particles into a mold. The metal particles can be in the form of a dry powder or a mixture that has been admixed with a binder in a mixing or kneading machine, or heated blender. When the metal particles are admixed with a binder prior to being injected into the mold, the mixing conditions can be selected based on various conditions such as particle diameters and shapes. In some cases, the binder at least partially coats or encapsulates the metal particles. Also, the binder may be disposed into the interstitial spaces between the metal particles by heating and mixing the binder with the particles. Alternatively, the metal particles and binder can be pelletized prior to being injected into the mold.

Since various types of metal powders that can be sintered are usable in the present invention, the metal particles can be selected from aluminum, nickel, titanium, copper, cobalt, stainless steel, and the like as well as various alloys thereof. However, since the green metal body will be sintered into an orthodontic bracket and/or base plate, it is preferable to use a dental-compatible material such as titanium, titanium alloy, and stainless steel. This is because the bracket needs to withstand the forces applied to the bracket by the archwire and/or ligatures that impart a high level of strain thereto. As such, the brackets should have a high level of strength and toughness so as not to be damaged during use. The metal is preferably safe for use in a person's mouth (i.e., having little or no toxicity). It is, of course, within the scope of the invention to coat the finished brackets with a protective coating in order to provide additional safety in the case where the metal used to make the brackets may not be safe if left uncoated.

A method of making a green metal body can also include injecting a binder into the mold in an amount sufficient to hold the metal particles together. As discussed, the binder can be premixed with the metal particles prior to injection. Alternatively, the binder and metal particles can be injected into a mold as different feed streams separately or simultaneously. When the metal particles and binder are not premixed, it may be advantageous for the binder to easily coat the particles by having a high work of adhesion with respect to the metal particles, or to be heated and mixed with the metal particles. Additionally, the dispersement of the binder within the metal particles can be enhanced by shaking or mixing the particles and binder after being injected into the mold.

The weight ratio of the metal particles and binder can vary depending on the molding conditions. For example, the metal to binder weight ratio can range from about 70:30 to about 98:2. Additionally, the weight ratio can range from about 75:25 to about 95:5. By setting the feed stock ratios within these ranges, a combined metal powder and binder feed can have moderate flowability, excellent molding properties, and can be formed into a green metal body that can be further processed in accordance with the present invention. However, it should be recognized that the characteristics of the optimal composition will depend on the type of metal particles and the type of binder as well as other variables in the process of making a green metal body.

A method of making a green metal body can also include forming a green metal body in the mold with the metal particles and binder. After the feed stock(s) are injected into the mold, the green metal body can be formed, for example, in an injection molding machine. The green body is formed by increasing the temperature and/or pressure so that the metal particles and binder are pressed together into the shape of the mold. Accordingly, the metal particles and binder can be set at temperature ranging from about 20° C. to about 380° C., and more preferable from about 8° C. to about 340° C. Also, the metal particles and binder can be pressed together at a pressure range of from about 2.9 MPa to about 200 MPa, or from about 19.6 MPa to about 100 MPa, depending on the binder-metal system.

The shape of the mold can be varied to accommodate a universal green metal body design or specific molds for each type of tooth. As such, a series of molds can be fabricated that correspond to different types of teeth to be used in forming a green metal body that corresponds to different types of teeth. Also, a series of molds can be generated for configuring the bonding surface of the brackets to fit teeth having a certain curvature. Alternatively, a substantially universal mold can be used to provide a rough shape that can be further processed into a green metal body shaped as an orthodontic bracket.

Accordingly, a method of making a green metal body also includes shaping the green metal body with a laser. Accordingly, a laser beam can be guided over the green metal body, where the path of the laser can be manually or computer controlled. Also, the path can be preset, or random depending on what portion of the green metal body is being cut. The laser can cut, melt and/or vaporize the metal particles and/or the binder to shape the green metal body.

In one embodiment, shaping the green metal body with a laser can result in a green metal body having the shape of an orthodontic bracket. Accordingly, a substantially rectangular green metal body can be cut with a laser to carve out the features described with respect to FIGS. 1 and 2. Such features that can be laser-cut into the green metal body can include tie wings, lobes, archwire slots, ligation grooves, self-ligating features, and the like. Thus, laser-shaping the green metal body can remove a substantial amount of metal particles from the green metal material and form the shape of an orthodontic bracket, including a self-ligating bracket.

Another embodiment of the present invention provides a method of forming a bonding surface (e.g., so as to have undercuts) in a green metal body having a shape of an orthodontic bracket. As such, a green metal body can be fabricated in accordance with the present invention. Alternatively, a green metal body in substantially a shape of an orthodontic bracket can be provided.

Additionally, a method of forming undercuts can include cutting undercuts into the base surface with a laser. The undercuts can be cut into the green metal body as described with respect to any shaping of the green metal body with a laser. In one embodiment, the undercuts, or any laser-cut portion, can have a relatively smooth topology, where the smoothness can result from fewer, smaller, or microscopic irregular elevations. Alternatively, the laser-cutting can be conducted to form the undercuts or any laser-shaped portion of the green metal body, specifically the bonding surface, to include a relatively rough topology.

Without being bound to any particular theory of laser-cutting phenomena, it is thought that the undercuts as well as the recesses can be formed in the surface of a green metal body by vaporizing, melting, and/or decomposing the organic binder with a laser. In this process, the laser is guided over the green metal body in a manner that melts, vaporizes, and/or decomposes the organic binder and ejects the metal particles from the green body from the point being hit by the laser. Additionally, the side wall of a recess or a protrusion can be hit with the laser to eject the green material therefrom, which can form additional recesses and undercuts therein. As such, the laser can be applied to the surface of the green metal body at various locations and at various angles in order to achieve the desired or programmed topology. Also, the size or depth of the features (e.g., protrusions, recesses, and undercuts) carved into base surface can be varied.

Depending on the temperature and/or duration of the laser over a particular location of the green metal body, it is possible to cleanly remove the metal particles from the green metal body. This occurs whenever the binder is melted, burned, or decomposed but the metal particles remain below their vaporization temperature. In such cases, the metal particles are ejected, fall off by gravity, or are otherwise removed from the green metal body entirely. It may also be possible to design a system in which at least a portion of the metal particles removed from the green metal body are re-deposited on the green body surface. This may occur, at least in theory, in the case where the metal particles are melted and/or vaporized but not ejected so far from the green metal body as to prevent the metal from re-solidifying and attaching itself to the green body surface. In the typical case, most or all of the metal particles will be removed cleanly from the green metal body and not become re-deposited.

The laser-cutting can be guided over the green metal body in a grid-like pattern to produce rows and columns of individual protrusions and individual recesses in a uniform pattern. As desired, the laser-cutting can be configured to carve precise cuts and features into the green metal body. Alternatively, other geometrical conformations can be created by accurately carving the green metal body with a laser such as identification indicia.

In one embodiment, a method of laser-cutting a green metal body can be conducted in a vacuum. This can allow for the ejected metal particles and/or binder to escape the surface without being re-deposited adjacent to the recess or undercut formed by the ejected material. In another embodiment, the laser-cut portion can be oriented facing down (inverted) so that any material ejected from the surface can fall away from and clear of the surface. When laser-cutting is performed with an inverted surface, the green metal body can be rotated so that each side of the orthodontic bracket that is being formed can have the extra green body materials fall free and clear of the external surface. Accordingly, the process of laser-shaping a green metal body can be preformed so that smooth surfaces and rounded features are formed in the external surface.

Another embodiment of the present invention provides a method of making an orthodontic bracket. Such a method can include making a green body, which can be comprised of injecting metal particles into a mold; injecting a binder into the mold in an amount sufficient to hold the metal particles together; forming, in the mold with the metal particles and binder, a green metal body; and shaping the green metal body with a laser. However, a green metal body in the shape of an orthodontic bracket, optionally, with undercuts formed in the base surface thereof can be provided. In either case, the method can include sintering the green metal body to obtain an orthodontic bracket.

Optionally, prior to sintering the green metal body a de-binding process can be carried out to remove the binder. As such, the de-binding can be performed by heat treatment in a non-oxidizing atmosphere, for instance, under a vacuum or in a low pressure condition. For example, the de-binding can be performed at about $1\times10^{-1}$ Torr (13.3 Pa) to about $1\times10^{-6}$ Torr ($1.3\times10^4$ Pa). Alternatively, the de-binding can be performed in nitrogen, argon, or other inert gas by melting, evaporating, or decomposing the binder. Additional de-binding conditions such as temperature increase rate or de-binding temperature can be modulated so as to avoid reactions with the metal particles. In one embodiment, the de-binding temperature can be within the range of about 150° C. to about 750° C.

The sintering can be performed at a low pressure from about $1\times10^{-1}$ Torr to about $1\times10^{-6}$ Torr, or in a vacuum or inert gas. As such, the green metal body can have the binder removed during the sintering process. Alternatively, the sintering process can remove a substantial amount, but not all of binder, where some of the binder can remain depending on the binding system. The sintering temperature can range from about 1000° C. to about 1500° C., or about 2400° C., and sintering times can range from about 0.5 hours to about 10 hours. However, sometimes sintering can last up to about 24 hours. Additionally, the sintering process should be modulated in order to grow metal powder grains into a dense sintered body. Accordingly, the sintered body should have a high density with a low porosity compared to the green metal body. Also, the sintered body can have a lower density and higher porosity compared to a cast metal.

When the green metal body is sintered, the volume shrinks as the porosity decreases and the density increases. As such, the green metal body can be fabricated and shaped to be larger than the resultant orthodontic bracket to accommodate for the volume lost during sintering. The volume decrease between the size of a green metal body and the size of a sintered orthodontic bracket can range from about 10% to about 30%. Typically, the volume decrease can be about 20%.

Since the volume of the green metal body decreases during sintering, various features of the green metal body can be fabricated to take shrinkage into account. This can allow for the laser-cut recesses and protrusions to be cut with a larger margin of error, or to cut larger recesses than will be present after the sintering process. Thus, when the green metal body is laser-cut the intricate shaping can result in even more precise and intricate features after sintering. Also, the manipulation of a larger green metal body can aid in handling and shaping the green metal body.

Another result of the shrinkage that occurs during sintering can include the topology of the sintered metal body being smoother compared to the green metal body prior to sintering. More particularly, when small or microscopic irregular elevations are formed during laser-cutting, these irregular elevations can be smoothed out during sintering. Additionally, the sintering can be carried out to round the larger or macroscopic irregular elevations. However, this smoothing effect does not necessarily have to remove the irregular elevations, but can create a better surface with less obtuse or sharp edges. As such, the smoothing effect can still retain the microscopic and/or macroscopic irregular elevations. On the other hand, the sintering process can be modulated to substantially remove the microscopic irregular elevations during the shrinkage, but it can retain the macroscopic irregular elevations. Alternatively, the macroscopic irregular elevations can be more rounded after sintering in comparison to the topology prior to sintering. Thus, at least one laser-cut portion on the exterior surface of the sintered metal body can have a smoother topology compared to at least one laser-cut portion on an exterior surface of the green metal body.

Accordingly, an orthodontic bracket can include a sintered metal body formed by sintering a green metal body comprised of a plurality of metal particles held together with a binder. The sintered metal body can include an exterior surface defining a shape of an orthodontic bracket. Also, at least one laser-cut portion on the exterior surface of the sintered metal body can be formed by cutting the green metal body with a laser.

When the green metal body is cut with a laser prior to sintering, the laser-cut portion on the sintered metal body can be substantially devoid of being charred by being cut with the laser before sintering. On the other hand, when a sintered piece is laser-cut, these portions on the sintered piece can be charred and rendered to be less biocompatible compared to an orthodontic bracket that was laser-cut before being sintered. This is because when a sintered metal body is cut with a laser, the cut portion can be charred, burned, and/or blackened by the process. Additionally, when a green metal body is cut with a laser, the laser-cut potions can similarly have charred portions. However, the laser-cut portion after sintering can be less charred than the same laser-cut portion on the green metal body prior to being sintered.

The sintering process and/or the de-binding process can function to partially de-char the metal particles, and hence the sintered metal body. Without being bound to theory, it is thought that when the binder melts or evaporates from the green metal body, the binder draws the charred material away from the green metal body. This can be because during sintering or de-binding, a portion of the binder will melt and flow over the laser-cut portion and leech the charred material away from the metal particles. Thus, laser-cut charring can be diminished by laser-cuffing a green metal body prior to sintering.

Also, without being bound to any particular theory, it is thought that an oxidized layer forms over the exterior surface of the green metal body as it is being sintered into an orthodontic bracket. Accordingly, laser shaping the green metal body prior to sintering can allow for the oxidized layer to form on the laser-cut portion of the exterior surface during sintering. The oxidized layer is thought to impart biocompatibility to the bracket. However, cutting (e.g., with a laser) a solid metal body can destroy the oxidized surface layer, and decrease biocompatibility. Thus, at least one laser-cut portion on the exterior surface of the sintered metal body can have a topology characterized by an oxidized surface formed by sintering, where the sintering is conducted after the green metal body has been laser-cut.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing an orthodontic appliance comprising:
    guiding a laser beam over a surface portion of a green body composed of particles held together by a binder in the shape of the orthodontic appliance to vaporize, melt, and/or decompose the binder at a point being hit by the laser beam;
    removing particles from the surface portion of the green body where the binder has been vaporized, melted, and/or decomposed to yield a laser-cut portion defined by the remaining particles of the green body, the laser-cut portion having a shape that is related to a negative shape of a lingual side or a buccal side of a tooth; and heating the green body to remove additional binder following removal of the binder during guiding of the laser beam over the surface portion, wherein heating includes sintering the particles together to form a sintered body including a sintered laser-cut portion that has the negative shape of the lingual side or the buccal side of the tooth so as to form a bonding surface of the orthodontic appliance, and wherein guiding the laser beam forms the laser-cut portion having at least one of a plurality of protrusions, recesses, and undercuts.

2. The method of claim 1, wherein the laser-cut portion includes identification indicia to identify a preselected tooth to which the laser-cut portion is to be mated, and wherein removing particles from the surface portion defines the identification indicia.

3. The method of claim 2, wherein the identification indicia include a numeral.

4. The method of claim 1, wherein guiding the laser beam includes guiding the laser beam according to a three-dimensional model of a particular patient's tooth.

5. The method of claim 1, wherein prior to guiding the laser beam, the method further includes ascertaining a three-dimensional model of the tooth and inputting the three-dimensional model into a computer.

6. The method of claim 1, wherein guiding the laser beam is computer controlled according to a three-dimensional model of a particular patient's tooth.

7. The method of claim 1, wherein removing particles from the surface portion determines at least one of a signing angulation and a slot position of the orthodontic appliance.

8. The method of claim 1, wherein the orthodontic appliance is a base plate configured to be attached to an orthodontic bracket.

9. The method of claim 1, wherein the orthodontic appliance is an orthodontic bracket configured to be attached to the tooth.

10. The method of claim 1, wherein the particles are metallic particles.

* * * * *